United States Patent [19]
Weinstock et al.

[11] 3,972,947
[45] Aug. 3, 1976

[54] PROCESS FOR THE PREPARATION OF CHLOROMETHYL METHYL ETHER

[75] Inventors: Leonard M. Weinstock, Belle Mead; Sandor Karady, Mountainside; Meyer Sletzinger, North Plainfield, all of N.J.

[73] Assignee: Merck & Co., Inc., Rahway, N.J.

[22] Filed: July 15, 1975

[21] Appl. No.: 596,559

Related U.S. Application Data

[63] Continuation-in-part of Ser. No. 439,676, Feb. 4, 1974, abandoned.

[52] U.S. Cl. .................. 260/614 R; 260/476 R; 260/488 R
[51] Int. Cl.² .................................... C07C 41/00
[58] Field of Search ............................ 260/614 R

[56] References Cited
UNITED STATES PATENTS
3,086,060  4/1963  Greer ........................... 260/614 R FOREIGN PATENTS OR APPLICATIONS
1,056,589  1/1967  United Kingdom ............ 260/614
210,852    2/1968  U.S.S.R. .......................... 260/614 R OTHER PUBLICATIONS
Kirk Othmer, Encyclopedia of Chemical Technology, John Wiley, New York, 2nd Ed. 1966, p. 96.
Baeyer, Ber 6, (1873), p. 221.
Buehler et al., Survey of Organic Synthesis, John Wiley, New York, 1970, pp. 310–311.

Primary Examiner—Howard T. Mars
Attorney, Agent, or Firm—Walter Patton; Julian S. Levitt

[57]  ABSTRACT

Single vessel, closed system, anhydrous, process for preparing high purity chloromethyl methyl ether comprising reacting methylal with hydrogen chloride; wherein said hydrogen chloride is generated, in situ, by contacting methanol, a reaction intermediate, with an acid chloride.

6 Claims, No Drawings

PROCESS FOR THE PREPARATION OF CHLOROMETHYL METHYL ETHER

This application is a continuation-in-part of our co-pending application Ser. No. 439,676, filed Feb. 4, 1974 now abandoned.

BACKGROUND OF THE INVENTION

This invention relates to a safe, highly efficient process for the preparation of chloromethyl methyl ether.

Chloromethyl methyl ether is a well known and valuable substance to the chemical industry. It is best known as a chloromethylating agent, a methoxymethylating agent and for its value in the form of a Grignard reagent, e.g., $CH_3OCH_2MgCl$, or as methoxymethyl lithium. Ubiquitous as chloromethyl methyl ether is, it is paradoxical that it is also extremely toxic and a known carcinogen.

Prior art methods for the preparation of chloromethyl methyl ether suffer from distinct disadvantages, for example: (1) typically the chloromethyl methyl ether product, is not of high purity, i.e., usually contaminated with dichloromethyl ether or water; (2) prior art processes are typically multistep or require steps which dangerously risk exposure of the toxic chloromethyl methyl ether to workers involved in its preparation; (3) typically a user of chloromethyl methyl ether must rely on distant producers for his requirements, thus dangerously running the risk of exposing the public to chloromethyl methyl ether in the event of mishap during shipment.

Thus, it is an object of the present invention to provide a safe and efficient method for the preparation of high purity chloromethyl methyl ether.

SUMMARY OF THE INVENTION

A process for preparing chloromethyl methyl ether comprising reacting methylal with HCl under anhydrous conditions, wherein said HCl is generated in situ by contacting methanol, a reaction intermediate with an acid chloride wherein the methylal and acid cloride are initially present in substantially equimolar amounts and HCl or methanol is introduced in trace quantities to initiate the reaction.

DETAILED DESCRIPTION OF THE INVENTION

The process invention may be depicted by the following overall reaction:

Wherein the term "acid chloride" is employed to describe reagents which are capable of yielding, in situ, HCl on contact with methanol. Such chlorinating agents for purposes of this invention are: organic acid chlorides,

wherein R is alkyl, or aryl and aralkyl such as phenyl, benzyl and the like and substituted derivatives thereof; and inorganic chlorinating agents such as thionyl chloride, sulfuryl chloride, phosphorous trichloride, phosphorous pentachloride, phosphorous oxychloride, phosgene and the like.

While the above reaction adequately describes the present invention, further insight may be obtained relative to the above-stated functional requirement of the chlorinating agent by stating the process invention mechanistically. Although, it is to be emphasized that Applicants are not limited by any theory, and that the following is intended solely for descriptive purposes.

When methylal and an equivalent amount of HCl are contacted, under anhydrous conditions, there is substantially no chloromethyl methyl ether formed since the equilibrium of the reaction lies far to the left as indicated by the heavy arrow in the following reaction:

$$CH_3OCH_2OCH_3 + HCl \rightleftarrows CH_3OCH_2Cl + CH_3OH \qquad (1)$$

Unexpectedly, it has been discovered that the equilibrium of the above reaction can be driven substantially quantitatively to the right in favor of the formation of chloromethyl methyl ether by the co-presence of a substantially equivalent amount (equivalence relative to the formation of $CH_3OCH_2Cl$) of an acid chloride of the above description.

The acid chloride drives the above equilibrium reaction (1) to the right in favor of chloromethyl methyl ether by two means. First, by reacting irreversibly with the methanol generated on the right hand side of the equilibrium reaction (1) to form a methyl ester and HCl. The consequence of removing the methanol from the right hand side of the equilibrium reaction (1) is to further drive the reaction to the right and thus to completion. The second means by which the acid chloride drives the equilibrium reaction (1) to the right is by regenerating the HCl which is being consumed on the left hand side of Equation (1). Thus, for purposes of illustration, taking the acid chloride to be an organic acid chloride,

the following mass action relationship provides the net reaction of the present invention:

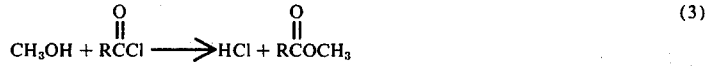

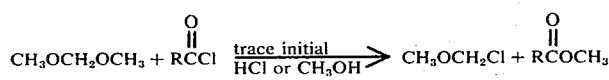  (4)

For purposes of the claimed invention, the phrase "trace initial [quantity of anhydrous] HCl" is defined to be from about 0.1 to about 10.0 mole % HCl based on the initial amount of methylal in the reaction mixture with the acid chloride. Such a quantity of HCl, per se, may be added at the start of the reaction, for example, as a gas; or may be formed according to Equation (3) by adding about 0.1 to about 10.0 mole % of a protic solvent such as, for example, a lower alkanol having from 1 to 5 carbon atoms. Methanol is preferred for this purpose. The preferred trace initial quantity of HCl or methanol is from about 1 to about 5 mole % of the initial concentration of methylal.

Thus in words, the net reaction (4) of the process of this invention comprises reacting methylal with a substantially equivalent amount of an acid chloride in the presence of a trace initial quantity of HCl or methanol to yield chloromethyl methyl ether and the corresponding methyl ester of the acid chloride.

The temperature of reaction may range from about 0° to about 100°C.; the preferred range is from about 20° to about 45°C. Typically the reaction is complete in from about 0.1 to about 50 hours with a yield of at least 95%. The reaction is capable of being conducted in a sealed vessel under anhydrous conditions, and, because of the extreme toxicity of chloromethyl methyl ether, such is preferred. A sealed reactions system also enhances the overall yield by keeping HCl in solution. Above 45°C. the reaction is strongly exothermic and accordingly, the acid chloride should be added in small portions commensurate with the reaction rate rather than introduced into the reaction vessel in one portion.

The methylal reactant is readily commercially available in reagent grade. Alternately, it may be prepared by a variety of well known processes such as the reaction of formaldehyde and methanol. It is preferred that the methylal be present at a slight excess, about 3–5 mole % relative to the chlorinating agent, to insure quantitative reaction of the chlorinating agent.

A solvent may be employed but in the most preferred embodiment of the process invention no solvent is employed, the reactants and products serving as their own reaction medium. If a solvent is employed, however, it must meet the requirements of being substantially inert to any of the above reactants or products and must possess appropriate solubility for the reactants and products. Suitable aprotic solvents include: ethers, for example ethyl ether, dioxane, tetrahydrofuran, and isopropylether; hydrocarbons, for examle, benzene, hexane, cyclohexane, toluene; and chlorinated solvents, for example, methylene chloride, chloroform, dichloroethane, and carbon tetrachloride.

No criticality exists as to the exact identity of the acid chloride other than the requirement that it liberate, in situ, HCl on contact with methanol. Suitable inorganic acid chlorides are thionyl chloride, sulfuryl chloride, phosphorous trichloride, phosphorous pentachloride, phosphorous oxychloride, phosgene, and the like. Suitable organic acid chlorides,

are those wherein R is lower alkyl having from 1 to about 10 carbon atoms; aryl or aralkyl having from 7 to about 20 carbon atoms such as phenyl, benzyl and nuclear substituted derivatives thereof. Lower alkyl acid chlorides having from 2 to about 7 carbon atoms, however, are preferred and, absent special requirements, acetyl chloride is most preferred.

When acetyl chloride is employed the corresponding methyl acetate product is compatible with the desired chloromethyl methyl ether product such that separation of the two is not required for the vast majority of purposes which require the use of chloromethyl methyl ether. Consequently, except in rare situations, it is not necessary to separate the chloromethyl methyl ether from the methyl acetate, thus avoiding excessive handling of the extremely toxic chloromethyl methyl ether. This compatibility (chloromethyl methyl ether—methyl ester) extends in general to other product mixtures obtained by reacting methylal with any of the above-mentioned acid chlorides. If desired, chloromethyl methyl ether may be separated from the ester product by distillation procedures well known in the art.

When it is desired to ultimately obtain substantially pure chloromethyl methyl ether, the process of the present invention is best performed by employing a relatively high molecular weight chlorinating agent,

wherein the R radical is substantially non polar so that the final separations procedure (extraction or distillation of the $CH_3OCH_2Cl$,

product mixture) may be conducted with enhanced efficiency and safety.

The following examples specifically illustrate, but do not limit, the process of this invention.

EXAMPLE 1

In a 100-ml. flask is charged 45 ml. methylal (0.51 moles), 35.3 ml. acetyl chloride (0.49 moles) and 1.2 ml. methanol (0.029 moles). The flask is sealed and allowed to stand at 25°C. The course of reaction is monitored periodically by assaying for acetyl chloride by nuclear magnetic resonance and vapor phase chromatography techniques run against known standards. After 24 hours less than 0.8% acetyl chloride remained unreacted and at 36 hours less than 0.5% acetyl chloride remained unreacted. The product comprising chloromethyl methyl ether (95% yield) and methyl acetate was stable against visible change for several days.

As in Example I substantially equivalent results are obtained when the acetyl chloride reactant is replaced by an equivalent amount of thionyl chloride, benzoyl chloride, and propionyl chloride, respectively, and when the 0.029 initial moles of methanol is replaced by 0.029 initial moles of ethanol, butanol, and cyclohexanol, respectively.

As in Example I, substantially equivalent results are obtained when the initial alcohol reactant is replaced by an equivalent molar amount of HCl (0.029 moles) which is introduced as a gas into the sealed reaction system and when the acetyl chloride reactant is replaced by an equivalent amount of the following acid chlorides: thionyl chloride, propionyl chloride, and benzoyl chloride, respectively.

What is claimed is:

1. A process for preparing chloromethyl methyl ether comprising reacting, at a temperature of from about 0° to about 100°C., in a sealed vessel under anhydrous conditions, methylal and an acid chloride wherein the acid chloride is selected from the group consisting of alkyl acid chlorides, aryl acid chlorides, aralkyl acid chlorides, thionyl chloride, sulfuryl chloride, phosphorous trichloride, phosphorous pentachloride, phosphorous oxychloride and phosgene; wherein the methylal is present from about 3 to about 5 mole % excess relative to the acid chloride, in the presence of an initial quantity of a substance selected from the group consisting of HCl and lower alkanol having from 1 to about 5 carbon atoms; wherein the initial quantity of HCl or lower alkanol is from about 0.1 to about 10% of the initial concentration of methylal.

2. The process of claim 1 wherein the alkyl acid chloride has from 2 to about 7 carbon atoms, and the aryl and aralkyl acid chloride has from 7 to about 20 carbon atoms.

3. The process of claim 2 wherein the alkyl acid chloride is acetyl chloride.

4. The process of claim 3 wherein the lower alkanol is methanol.

5. The process of claim 4 wherein the amount of methanol is from about 1 to about 5 mole % of the initial methylal concentration.

6. The process of claim 5 wherein the temperature is from about 20° to about 45°C.

* * * * *